United States Patent [19]

McClelland et al.

[11] Patent Number: 5,859,212

[45] Date of Patent: Jan. 12, 1999

[54] METHOD OF ISOLATING AND PURIFYING SICAM-1

[75] Inventors: Alan McClelland, Old Saybrook; Jeffrey M. Greve, Branford, both of Conn.

[73] Assignee: Bayer Corporation, West Haven, Conn.

[21] Appl. No.: 443,966

[22] Filed: May 18, 1995

Related U.S. Application Data

[62] Division of Ser. No. 425,989, Apr. 20, 1995, which is a continuation of Ser. No. 156,653, Nov. 22, 1993, abandoned, which is a continuation of Ser. No. 5,204, Jan. 15, 1993, abandoned, which is a continuation of Ser. No. 449,356, Dec. 21, 1989, abandoned, which is a continuation-in-part of Ser. No. 445,951, Dec. 13, 1989, abandoned, which is a continuation-in-part of Ser. No. 301,192, Jan. 24, 1989, Pat. No. 5,235,049.

[51] Int. Cl.$^6$ ........................................................ C07K 1/22
[52] U.S. Cl. ........................ 530/413; 530/412; 530/391.1
[58] Field of Search ..................................... 530/413, 412, 530/388.22, 388.73

[56] References Cited

U.S. PATENT DOCUMENTS 5,235,049  8/1993  McClelland et al. .

*Primary Examiner*—Lila Feisee
*Assistant Examiner*—Phillip Gambel

[57] ABSTRACT

The present invention relates to a soluble form of-intercellular adhesion molecule (sICAM-1) and purified and isolated human sICAM-1. This invention also relates to a purified and isolated DNA sequence encoding sICAM-1. The extracellular domain of sICAM-1 and insoluble ICAM-1 are substantially the same. ICAM-1 is involved in the process through which lymphocytes attach to cellular substrates during inflammation and serves as the major human rhinovirus receptor (HRR). sICAM-1 therefore has both the property of reducing immune inflammation and inhibiting infection of rhinovirus and Coxsackie A virus.

6 Claims, 8 Drawing Sheets

```
58   ATGGCTCCCAGCAGCCCCCGGCCCGCGCTGCCCGCACTCCTGGTCCTGCTCGGGGCTCTG   117
     M   A   P   S   S   P   R   P   A   L   P   A   L   L   V   L   L   G   A   L

118  TTCCCAGGACCTGGCAATGCCCAGACATCTGTGTCCCCCTCAAAAGTCATCCTGCCCCGG   177
     F   P   G   P   G   N   A   Q   T   S   V   S   P   S   K   V   I   L   P   R    13

178  GGAGGCTCCGTGCTGGTGACATGCAGCACCTCCTGTGACCAGCCCAAGTTGTTGGGCATA   237
     G   G   S   V   L   V   T   C   S   T   S   C   D   Q   P   K   L   L   G   I    33

238  GAGACCCCGTTGCCTAAAAAGGAGTTGCTCCTGCCTGGGAACAACCGGAAGGTGTATGAA   297
     E   T   P   L   P   K   K   E   L   L   L   P   G   N   N   R   K   V   Y   E    53

298  CTGAGCAATGTGCAAGAAGATAGCCAACCAATGTGCTATTCAAACTGCCCTGATGGGCAG   357
     L   S   N   V   Q   E   D   S   Q   P   M   C   Y   S   N   C   P   D   G   Q    73

358  TCAACAGCTAAAACCTTCCTCACCGTGTACTGGACTCCAGAACGGGTGGAACTGGCACCC   417
     S   T   A   K   T   F   L   T   V   Y   W   T   P   E   R   V   E   L   A   P    93

418  CTCCCCTCTTGGCAGCCAGTGGGCAAGAACCTTACCCTACGCTGCCAGGTGGAGGGTGGG   477
     L   P   S   W   Q   P   V   G   K   N   L   T   L   R   C   Q   V   E   G   G   113

478  GCACCCCGGGCCAACCTCACCGTGGTGCTGCTCCGTGGGGAGAAGGAGCTGAAACGGGAG   537
     A   P   R   A   N   L   T   V   V   L   L   R   G   E   K   E   L   K   R   E   133

538  CCAGCTGTGGGGGAGCCCGCTGAGGTCACGACCACGGTGCTGGTGAGGAGAGATCACCAT   597
     P   A   V   G   E   P   A   E   V   T   T   T   V   L   V   R   R   D   H   H   153

598  GGAGCCAATTTCTCGTGCCGCACTGAACTGGACCTGCGGCCCCAAGGGCTGGAGCTGTTT   657
     G   A   N   F   S   C   R   T   E   L   D   L   R   P   Q   G   L   E   L   F   173

658  GAGAACACCTCGGCCCCCTACCAGCTCCAGACCTTTGTCCTGCCAGCGACTCCCCCACAA   717
     E   N   T   S   A   P   Y   Q   L   Q   T   F   V   L   P   A   T   P   P   Q   193

718  CTTGTCAGCCCCCGGGTCCTAGAGGTGGACACGCAGGGGACCGTGGTCTGTTCCCTGGAC   777
     L   V   S   P   R   V   L   E   V   D   T   Q   G   T   V   V   C   S   L   D   213

778  GGGCTGTTCCCAGTCTCGGAGGCCCAGGTCCACCTGGCACTGGGGGACCAGAGGTTGAAC   837
     G   L   F   P   V   S   E   A   Q   V   H   L   A   L   G   D   Q   R   L   N   233
```

FIG.1A [SEQ ID NO: 10]

```
838   CCCACAGTCACCTATGGCAACGACTCCTTCTCGGCCAAGGCCTCAGTCAGTGTGACCGCA   897
      P  T  V  T  Y  G  N  D  S  F  S  A  K  A  S  V  S  V  T  A    253

898   GAGGACGAGGGCACCCAGCGGCTGACGTGTGCAGTAATACTGGGGAACCAGAGCCAGGAG   957
      E  D  E  G  T  Q  R  L  T  C  A  V  I  L  G  N  Q  S  Q  E    273

958   ACACTGCAGACAGTGACCATCTACAGCTTTCCGGCGCCCAACGTGATTCTGACGAAGCCA   1017
      T  L  Q  T  V  T  I  Y  S  F  P  A  P  N  V  I  L  T  K  P    293

1018  GAGGTCTCAGAAGGGACCGAGGTGACAGTGAAGTGTGAGGCCCACCCTAGAGCCAAGGTG   1077
      E  V  S  E  G  T  E  V  T  V  K  C  E  A  H  P  R  A  K  V    313

1078  ACGCTGAATGGGGTTCCAGCCCAGCCACTGGGCCCGAGGGCCCAGCTCCTGCTGAAGGCC   1137
      T  L  N  G  V  P  A  Q  P  L  G  P  R  A  Q  L  L  L  K  A    333

1138  ACCCCAGAGGACAACGGGCGCAGCTTCTCCTGCTCTGCAACCCTGGAGGTGGCCGGCCAG   1197
      T  P  E  D  N  G  R  S  F  S  C  S  A  T  L  E  V  A  G  Q    353

1198  CTTATACACAAGAACCAGACCCGGGAGCTTCGTGTCCTGTATGGCCCCCGACTGGACGAG   1257
      L  I  H  K  N  Q  T  R  E  L  R  V  L  Y  G  P  R  L  D  E    373

1258  AGGGATTGTCCGGGAAACTGGACGTGGCCAGAAAATTCCCAGCAGACTCCAATGTGCCAG   1317
      R  D  C  P  G  N  W  T  W  P  E  N  S  Q  Q  T  P  M  C  Q    393

1318  GCTTGGGGGAACCCATTGCCCGAGCTCAAGTGTCTAAAGGATGGCACTTTCCCACTGCCC   1377
      A  W  G  N  P  L  P  E  L  K  C  L  K  D  G  T  F  P  L  P    413

1378  ATCGGGGAATCAGTGACTGTCACTCGAGATCTTGAGGGCACCTACCTCTGTCGGGCCAGG   1437
      I  G  E  S  V  T  V  T  R  D  L  E  G  T  Y  L  C  R  A  R    433

1438  AGCACTCAAGGGGAGGTCACCCGCAAGCCCCCGGTATGAGATTGTCATCATCACTGTGG   1497
      S  T  Q  G  E  V  T  R  K  P  P  G  M  R  L  S  S  S  L  W    453

1498  TAG  1500
      *
```

FIG. 1B [SEQ ID NO: 10] (con't)

COMPARISON OF C-TERMINAL REGIONS OF ICAM-1 AND sICAM-1

```
1441  ACTCAAGGGGAGGTCACCCGCAAGGTGACCGTGAATGTGCTCTCCCCCCGGTATGAGATT
 435   T  Q  G  E  V  T  R  K  V  T  V  N  V  L  S  P  R  Y  E  I

1441  ACTCAAGGGGAGGTCACCCGCAAG-------------------CCCCCCGGTATGAGATT
 435   T  Q  G  E  V  T  R  K                    P  P  G  M  R  L

1501  GTCATCATCACTGTGGTAGCAGCCGCAGTCATAATGGGCACTGCAGGCCTCAGCACGTAC
 455   V  I  I  T  V  V  A  A  A  V  I  M  G  T  A  G  L  S  T  Y

1482  GTCATCATCACTGTGGTAGCAGCCGCAGTCATAATGGGCACTGCAGGCCTCAGCACGTAC
 449   S  S  S  L  W  *

1561  CTCTATAACCGCCAGCGGAAGATCAAGAAATACAGACTACAACAGGCCCAAAAAGGGACC
 475   L  Y  N  R  Q  R  K  I  K  K  Y  R  L  Q  Q  A  Q  K  G  T

1542  CTCTATAACCGCCAGCGGAAGATCAAGAAATACAGACTACAACAGGCCCAAAAAGGGACC

1621  CCCATGAAACCGAACACACAAGCCACGCCTCCCTGAACCTATCCCGGGACAGGGCCTCTT
 495   P  M  K  P  N  T  Q  A  T  P  P  *

1602  CCCATGAAACCGAACACACAAGCCACGCCTCCCTGAACCTATCCCGGGACAGGGCCTCTT
```

UPPER LINES: ICAM-1 cDNA SEQUENCE AND TRANSLATION [SEQ ID NO:11]

LOWER LINES: sICAM-1 cDNA SEQUENCE AND TRANSLATION [SEQ ID NO:12]

FIG.2

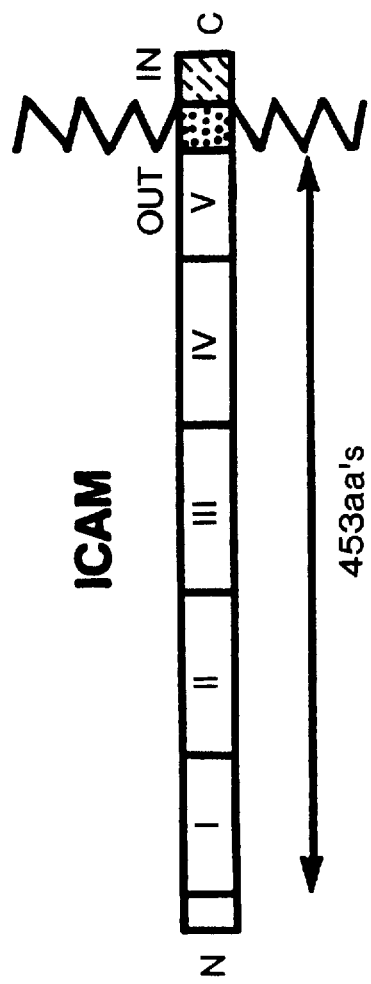
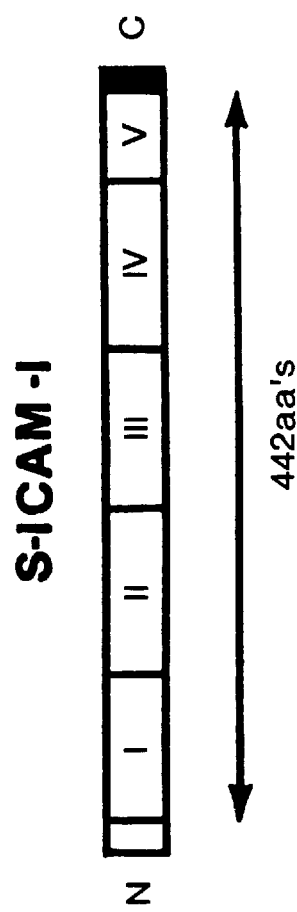

1  2  3

- -23
- -9.4
- -6.6
- -4.4
- -2.3
- -2.0

1  2  3

- -28S
- -18S 1  2  3

- ∕2323
- -1929
- -1371
- -1264
- -702

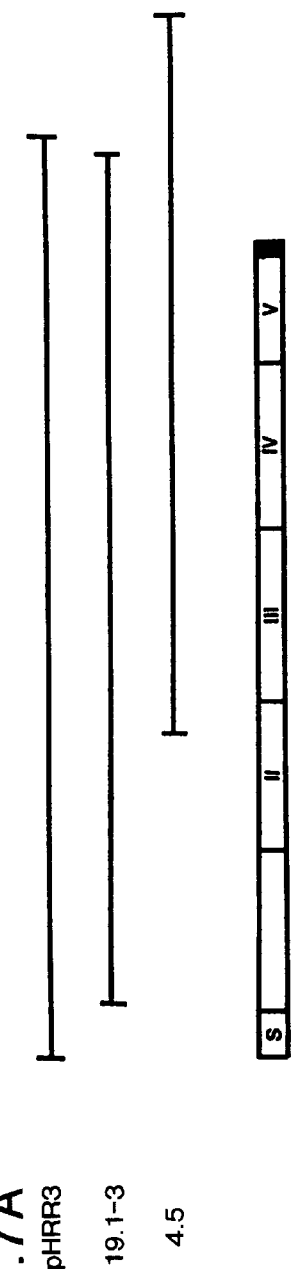
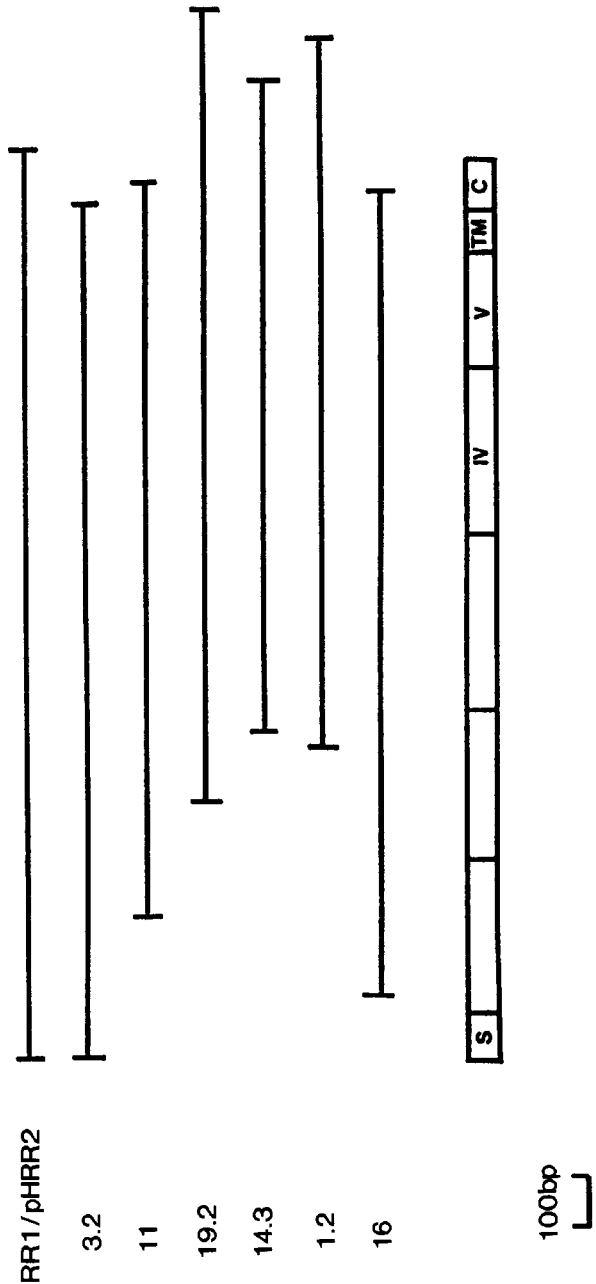
FIG.7A
FIG.7B

METHOD OF ISOLATING AND PURIFYING SICAM-1

This is a divisional of copending application U.S. Ser. No. 08/425,989 filed Apr. 20, 1995, which is a continuation of U.S. Ser. No. 08/156,653 filed Nov. 22, 1993, now abandoned, which is a continuation of U.S. Ser. No. 08/005,204 filed Jan. 15, 1993, now abandoned, which is a continuation of U.S. Ser. No. 07/449,356 filed Dec. 21, 1989, now abandoned, which is a continuation-in-part of U.S. Ser. No., and a continuation-in-part of U.S. Ser. No. 07/445,951 filed Dec. 13, 1989, now abandoned, which is a continuation-in-part of U.S. Ser. No. 07/301,192 filed Jan. 24, 1989, which issued as U.S. Pat. No. 5,235,049 on Aug. 10, 1993.

BACKGROUND OF THE INVENTION

The present invention relates to a soluble form of intercellular adhesion molecule (sICAM-1) as well as the DNA sequence encoding sICAM-1. sICAM-1 and ICAM-1 have substantial similarity, in that they share the first 442 $NH_2$-terminal amino acids of the extracellular domain. However, sICAM-1 differs from ICAM-1 at the C-terminus, and these changes confer solubility to sICAM-1. ICAM-1 is known to mediate adhesion of many cell types, including endothelial cells, to lymphocytes which express lymphocyte function-associated antigen-1 (LFA-1). ICAM-1 has the property of directly binding LFA-1. There is also evidence for LFA-1 mediated adhesion which is not via ICAM-1. Additionally, ICAM-1 has the ability to bind both LFA-1 and human rhinovirus. It has the property of inhibiting infection of rhinovirus and Coxsackie A viruses. It may be used to antagonize adhesion of cells mediated by ICAM-1 binding including ICAM-1/LFA-1 binding and thus be useful in treatment of inflammation, graft rejection, LFA-1 expressing tumors, and other processes involving cell adhesion. Based on the substantial similarity of the extracellular domains of ICAM-1 and sICAM-1, sICAM-1 has the properties identified for ICAM-1.

The major Human Rhinovirus Receptor (HRR) has been transfected, identified, purified and reconstituted as described in co-pending U.S. patent applications Ser. No. 262570 and 262428 filed Oct. 25, 1988. This receptor has been shown to be identical to a previously described cell surface protein, ICAM-1. European Patent Application 0 289 949 describes a membrane associated cell adhesion molecule (ICAM-1) which mediates attachment of many cell types including endothelial cells to lymphocytes which contain LFA-1. This patent application provides a discussion of the present research in the field of intercellular adhesion molecules. It is important to note that the inventors specifically looked for an alternatively spliced mRNA for ICAM-1 and did not identify one. ICAM-1 was first identified based on its role in adhesion of leukocytes to T-cells (Rothlein, R. et al, *J. Immunol.* 137: 1270–1274 (1986)) which has been shown to be mediated by the heterotypic binding of ICAM-1 to LFA-1 (Marlin et al, *Cell* 51: 813–819 (1987)). The primary structure of ICAM-1 has revealed that it is homologous to the cellular adhesion molecules Neural Cell Adhesion Molecule (NCAM) and Mylein-Associated Glycoprotein (MAG), and has led to the proposal that it is a member of the immunoglobulin supergene family (Simmons et al, *Nature* 331: 624–627 (1988); Staunton et al, *Cell* 52: 925–933 (1988) The DNA sequence of cDNA clones are described in the above referenced papers by Simmons et al and Staunton et al, supra, from which the amino acid sequence of ICAM-1 can be deduced. The ICAM-1 molecule has a typical hydrophobic membrane spanning region containing 24 amino acids and a short cytoplasmic tail containing 28 amino acids. The ICAM-1 of the prior art is an insoluble molecule which is solubilized from cell membranes by lysing the cells in a non-ionic detergent. The solubilized ICAM-1 mixture in detergent is then passed through a column matrix material and then through a monoclonal antibody column matrix for purification.

SUMMARY OF THE INVENTION

The present invention provides an endogenous alternatively spliced molecular species of ICAM-1 designated sICAM-1 which displays an alternative mRNA sequence and which is soluble without the addition of a detergent.

The present invention provides purified and isolated human soluble intercellular adhesion molecule (sICAM-1), or a functional derivative thereof, substantially free of natural contaminants. sICAM-1 can be obtained from HeLa, HE1 and primary transfectant cells thereof characterized by being soluble in the absence of nonionic detergents and being the translation product defined by a novel mRNA sequence. This natural product of human cells has the advantage of being secreted from cells in a soluble form and not being immunogenic. The natural soluble product differs from the natural insoluble product in that the soluble product contains a novel sequence of 11 amino acid residues at the C-terminus and does not contain the membrane spanning and cytoplasmic domains present in the insoluble form.

The present invention provides a purified and isolated DNA sequence encoding sICAM-1 as well as a host cell encoding said sequence.

The present invention provides a method of recovering soluble intercellular adhesion molecule in substantially pure form comprising the steps of:

(a) removing the supernatant from unlysed cells,
(b) introducing the supernatant to an affinity matrix containing immobilized antibody capable of binding to sICAM-1,
(c) permitting said sICAM-1 to bind to said antibody of said matrix,
(d) washing said matrix to remove unbound contaminants, and
(e) recovering said sICAM-1 in substantially pure form by eluting said sICAM-1 from said matrix.

Further purification utilizing a lectin or wheat germ agglutinin column may be used before or after the antibody matrix step. Other purification steps could include sizing chromatography, ion chromatography, and gel electrophoresis. Further purification by velocity sedimentation through sucrose gradients may be used. The antibody capable of binding to sICAM-1 could include antibodies against ICAM-1 or HRR.

The present invention includes polyclonal antibodies against sICAM-1.

The present invention further includes an antibody specific for sICAM-1, capable of binding to the sICAM-1 molecule and that is not capable of binding to ICAM-1. For a method for producing a peptide antisera see Green et al, Cell 28: 477–487 (1982).

The invention also includes a hybridoma cell line capable of producing such an antibody.

This invention further includes the therapeutic use of antibodies specifically directed to sICAM-1 to increase the adhesion of cells mediated by ICAM-1 and LFA-1.

The invention further includes a method for producing an antibody which is capable of binding to sICAM-1 and not to ICAM-1 comprising the steps of (a) preparing a peptide-protein conjugate said peptide-protein conjugate specific to at least a portion of the unique 11 amino acid sequence present in sICAM-1, (b) immunizing an animal with said peptide-protein conjugate, (c) boosting the animals, and (d) obtaining the antisera.

The antibodies would be capable of binding to sICAM-1 and not capable of binding to ICAM-1. The invention includes the hybridoma cell line which produces an antibody of the same specificity, the antibody produced by the hybridoma cell and the method of production.

The invention further includes a method of inhibiting lymphocyte function associated antigen (LFA-1) and intercellular adhesion molecule-1 (ICAM-1) interaction comprising the step of contacting LFA-1 containing cells with sICAM-1 or a functional derivative thereof. This method of inhibition of ICAM-1 adhesion has application in such disease states as inflammation, graft rejection, and for LFA-1 expressing tumor cells.

This invention further includes a method of diagnosis of the presence and location of an LFA-1 expressing tumor cell.

This invention further includes a method for substantially reducing the infection of human rhinoviruses of the major receptor group comprising the step of contacting the virus with sICAM-1 or a functional derivative thereof.

BRIEF DESCRIPTION OF THE DRAWINGS

FIG. 1, parts A and B, shows the nucleotide and amino acid sequence of sICAM-1.

FIG. 2 is a comparision of the C-terminal regions of sICAM-1 and ICAM-1. The nucleotide and deduced amino acid sequences of ICAM-1 and sICAM-1 are shown beginning at amino acid residue 435. Dashes in the sICAM-1 sequence indicate missing nucleotides. The positions of the stop codons in both proteins are indicated by an asterisk.

FIGS. 3A and B are comparison of the structure of sICAM-1 and ICAM-1. The membrane spanning region of ICAM-1 is indicated by the stippled box and the cytoplasmic domain by the hatched box. The novel C-terminus of sICAM-1 is indicated by the solid box. The five predicted domains showing homology with immunoglobulin are numbered I to V.

FIG. 4A: Southern blot of HeLa (Lane 1), LTK- (Lane 2) and HE1 (Lane 3) DNA restricted with Eco R1 and probed with the oligonucleotide ICAM-1.

FIGS. 7A and 7B are a graphical representation of the cloned sICAM-1 and ICAM-1 plasmids.

FIG. 7A pHRR3 is a full length cDNA encoding sICAM-1 obtained by PCR. Clones 19.1-3 and 4.5 are partial cDNA clones encoding sICAM-1 obtained from an HE1 cDNA library in lambda GT11. Beneath the clones is a schematic of the sICAM-1 molecule. S denotes the signal peptide and I to V the IgG homologous domains. The solid box indicates the unique 11 amino acid C-terminus.

FIG. 7B pHRR1 and pHRR2 are full length ICAM-1 cDNA clones obtained by PCR. The remaining ICAM-1 clones were obtained from an HE1 cDNA library in lambda GT11. Beneath the clones is a schematic of the ICAM-1 molecule, showing the signal peptide (S), the five IgG homologous domains (I to V), the transmembrane region (TM) and the cytoplasmic domain (C).

DESCRIPTION OF THE PREFERRED EMBODIMENTS

Figure 4A:
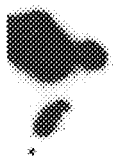
FIGS. 4A, B, and C show the ICAM-1 gene and its expression in HRR transfectants.

One aspect of the present invention relates to the discovery of a soluble natural binding ligand to the receptor binding site of Human Rhinovirus (HRV) and which also binds to LFA-1. This soluble natural molecule is related to but distinct from the molecule designated "Intercellular Adhesion Molecule-1" or "ICAM-1" which is insoluble, bound to the cell membrane and possesses a typical hydrophobic membrane spanning region and a short cytoplasmic tail. The novel protein of the present invention has a DNA sequence which includes a significant difference from the published DNA sequence for ICAM-1. sICAM-1 contains most of the extracellular domain of ICAM-1, which includes the functional domains for multiple functions including HRV and LFA-1 binding, but lacks the membrane spanning and cytoplasmic domains. sICAM-1 retains the ability to bind HRV and LFA-1 and is secreted in a soluble form. The DNA sequence for sICAM-1 contains a deletion of 19 base pairs from nucleotide 1465 to 1483 according to the numbering of Staunton et al, supra (1988). The remainder of the sICAM-1 clone matches the published ICAM-1 sequence with the exception of a substitution of an A for G at nucleotide position 1462 which changes Glu 442 to Lys, as shown in FIG. 1. The sequence of amino acid residues in a peptide is designated in accordance with standard nomenclature such as Lehninger's *Biochemistry*, Worth Publishers, New York, N.Y. (1970). sICAM-1 is a natural product of HeLa and HE1 cells and other human cells which should have the property of binding to and inhibiting the infection of human rhinovirus and Coxsackie A viruses. It also has the property of binding to LFA-1 and may be used to antagonize adhesion of cells mediated by ICAM-1/LFA-1 binding and thus be useful as a therapeutic in treatment of inflammation, graft rejection, suppression of LFA-1 expressing tumor cells and other processes involving cell adhesion. Isolated and purified sICAM-1 protein as a therapeutic would not possess the immunogenic problems associated with foreign proteins.

The secretion of a soluble naturally occurring protein eliminates the problems associated with production and purification of an insoluble, cell membrane bound protein, since cell lysis is not required and thus continuous culture can be employed as well as simplified procedures for purification and isolation of sICAM-1.

Non-human mammalian cell lines which express the major human rhinovirus receptor gene have been previously identified and are the subject matter of copending U.S. patent application Ser. No. 262,570 and 262,428 filed Oct. 25, 1988, and include references to the ATCC deposits for the cell lines. The major human rhinovirus receptor was identified with monoclonal antibodies which inhibit rhinovirus infection. These monoclonal antibodies recognized a 95 kd cell surface glycoprotein on human cells and on mouse transfectants expressing a rhinovirus-binding phenotype. Purified 95 Kd protein binds to rhinovirus in vitro. Protein sequence from the 95 kd protein showed an identity with that of ICAM-1; a cDNA clone obtained from mouse transfectants expressing the rhinovirus receptor had the same sequence published for ICAM-1, except for the A for G change previously described. Thus it was determined that the major human rhinovirus receptor and ICAM-1 were the same protein. A transfected mouse L-cell line designated HE1 had been isolated which contained and expressed the HRR gene or ICAM-1 gene. The ICAM-1 terminology has been used although it is now recognized that HRR and ICAM-1 are interchangeable.

A randomly primed cDNA library was prepared in lambda GT11 from HE1 polyA+ RNA. The library was screened in duplicate using two oligonucleotides derived from the published sequence of ICAM-1. Oligonucleotide ICAM-1 has the sequence GAGGTGTTCTCAAACAGCTCCAGCCCTTGGGGCCGCAGGTCCAGTTC SEQ ID NO:5 and oligonucleotide ICAM-3 has the sequence CGTTGGCAG GACAAAGGTCTGGAGCTGGTAGGGGGCCGAGGT GTTCT SEQ ID NO:6.

Eight positive clones were obtained from one screen and three were selected for further study. DNA sequencing of two of the clones showed identity with the published ICAM-1 sequence. The sequence of the third clone, lambda 19.1-3 was significantly different from the other two clones in that there was a deletion of 19 bp from nucleotide 1465 to 1483 according to the numbering of Staunton et al. supra. The 19 bp deletion was present in a second cDNA, lambda HE1-4.5 and independently confirmed using polymerase chain reaction (PCR) generated cDNA. Analysis of the cDNA sequence predicted the existence of a secreted form of ICAM-1 that is generated by an alternative splicing mechanism. Western blot identification of sICAM-1 from culture supernatants of HE1 and HeLa cell lines confirm that the sICAM-1 mRNA sequence encodes a soluble form of ICAM-1 that does not associate with the cell surface but is released into the cell medium. An alternatively spliced mRNA generating a secreted form of another adhesion molecule (NCAM) has been identified (Glower et al, Cell 55:955–964 (1988)), although in NCAM an exon is incorporated into the mRNA while in the present invention an exon is deleted from the mRNA. No alternative mRNA sequence for ICAM-1 had previously been identified. (Staunton et al.)

sICAM-1 cDNA Clones

Figure 4B:
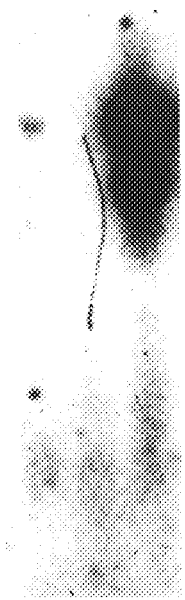
FIG. 4B: Northern blot of HeLa (Lane 1), Lkt$^{31}$ (Lane 2), and HE1 (Lane 3). poly A+ RNA probed with the oligonucleotide ICAM-1.
Figure 4C:
FIG. 4C: PCR amplification of cDNA prepared from HeLa (Lane 1), Ltk$^-$ (Lane 2) and HE1 (Lane 3) poly A+ RNA. The primers used were from the N-terminal and C-terminal coding regions of ICAM-1 having the sequence ggaattcATGGCTCCCAGCAGCCCCCG-GCCC SEQ ID NO:1 and ggaattcTCAGGGAGGCGTG-GCTTGTGTGTT SEQ ID NO:2. Upper case denotes ICAM-1 sequence, lower case restriction site linkers. Lanes 1 and 2, 72 hour exposure, Lane 3, 90 minute exposure.
Figure 5:
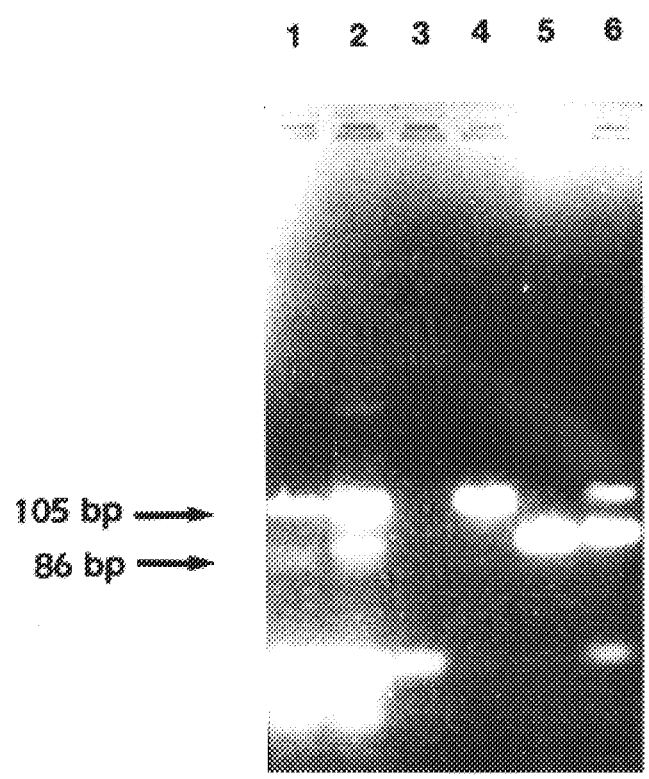
FIG. 5 is a gel showing the detection of the ICAM-1 and sICAM-1 mRNAs in HeLa and HE1 cells. PCR amplification was performed on 100ng single stranded cDNA using the primers PCR 5.4 (CTTGAGGGCACCTACCTCTGTCGG) SEQ ID NO:3 and PCR 3.4 (AGTGATGATGACAATCTCATACCG) SEQ ID NO:4. Extensions were performed at 72° C. for 25 cycles and one tenth of the product was analysed on a 1% agarose/ 3% NuSieve® gel FMC, Rockland, Me. Lane 1, HeLa cDNA; lane 2, HE1 cDNA; lane 3, LTK$^-$ cDNA; lane 4, ICAM-1 phage control;, lane 5, sICAM-1 phage control; lane 6, ICAM-1+sICAM-1 phage control. Specific amplification products of 105 bp and 86 bp are indicated by the arrows.
Figure 6:
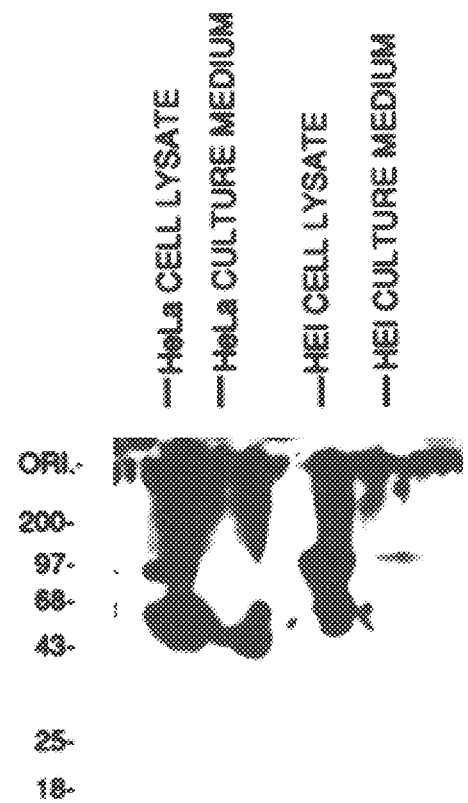
FIG. 6 is a Western blot showing the synthesis of a soluble form of ICAM-1 protein by HeLa and HE1 cells. It demonstrates the existence of a protein species in the culture supernatant of HeLa and HE1 cells related to ICAM-1. Equivalent aliquots of-cell lysates and culture supernatants were separated by SDS-PAGE, blotted onto nitrocellulose, and probed with a rabbit polyclonal antisera to ICAM-1 followed by $^{125}$I protein A; a species migrating close to the position of membrane-bound ICAM-1 is seen in both HeLa and HE1 culture supernatants.

A randomly primed cDNA library was constructed in lambda GT11 from HE1 poly A+ by Clontech Laboratories, Palo Alto, Calif. The library was screened with two 47 mer oligonucleotide probes from the middle of the ICAM-1 coding sequence. A positive clone designated 19.1-3 was isolated which had an insert of 1.5 kb; a second cDNA clone designated 4.5 which has an insert of 1.25 kb was isolated; and an additional cDNA clone pHRR-3 was obtained by subcloning the products of PCR amplification into Bluescript® utilizing the Perkin-Elmer/Cetus DNA Amplification System, Perkin Elmer, Wellesley Mass., as shown in FIG. 4C, lane 3. These clones showed a significant difference from the published ICAM-1 sequence. They all contain a deletion of 19 base pairs from nucleotide 1465 to 1483 according to the numbering of Staunton et al, supra. In order to demonstrate directly that the s-ICAM mRNA is present in HE1 cells and HeLa cels, a PCR experiment was performed using primers which flank the 19 bp region which is absent from the s-ICAM mRNA (FIG. 8). Using these primers the product from the ICAM-1 mRNA is 105 bp while the s-ICAM-1 product is 19 bp shorter i.e. 86 bp. This experiment shows that both HE1 cells and HeLa cells contain both forms of the ICAM-1 mRNA while the control L-cells do not. A synthetic oligonucleotide designated PCR3.2 having the following sequence:
ggaattcTCACTCATACCGGGGGGAGAGCACATT [SEQ ID NO:7]
was used to distinguish between cDNA clones containing the 19 bp deletion from clones not containing the 19 bp deletion. The synthetic oligonucleotide does not bind to cDNA clones which contain the 19 bp deletion. In addition, partial sequence of the cDNA 19.1-3 and PHRR-3 confirmed the 19 bp deletion. This data indicates that there are at least two different and distinct ICAM-1 species in HE1 cells. The insoluble ICAM-1 of the prior art and a novel soluble form as described in the present invention.

The sequences of the deleted (sICAM-1) and the nondeleted (ICAM-1) forms of the Intercellular Adhesion Molecule-1 mRNA represented by the cDNA clones are shown in FIG. 2. The sequence at the point of deletion is AGGT consistent with an RNA splice junction. The removal of 19 bases from the mRNA shifts the reading frame and causes the two polypeptide sequences to diverge at amino acid residue 443. The deleted form (sICAM-1) contains an additional 11 residues followed by an in-frame termination codon. This molecule thus consists of 453 amino acids as compared to 505 amino acids for the nondeleted form. Beginning with the N-terminus of ICAM-1, sICAM-1 has 442 amino acids in common with ICAM-1. The deleted form (sICAM-1) contains a unique 11 amino acid C-terminus but lacks the membrane spanning (24 amino acids) and cytoplasmic tail 28 amino acids) domains of ICAm-1, as shown in FIG. 3.

ICAM-1 cDNA Clones

A plurality of methods may be used to clone genes. One method is to use two partially overlapping 47 mer oligonucleotide probes. These two probes termed oligonucleotide ICAM-1 and oligonucleotide ICAM-3 were synthesized from the published ICAM-1 sequence. The ICAM-1 oligonucleotide was labeled to high specific activity and hybridized to a Southern blot under high stringency conditions. As shown in FIG. 4A, a single band of 4.4 kb was detected in HeLa, HE1 and two primary HRR transfectant cell lines and was absent from Ltk⁻ cells. This result confirms that the HRR transfectants contain the human ICAM-1 gene. The size of the fragment agrees with Simmons et al but differs from Staunton et al probably reflecting a restriction site polymorphism.

The ICAM-1 oligonucleotide was used to probe a Northern blot of poly A+ RNA from the same cell lines. As shown in FIG. 4B, an mRNA of 3.3 kb was detected in HeLa, HE1, and primary transfectant cell lines but was absent from Ltk⁻ cells. The signal in HE1 cells was many times stronger than the other cell lines indicating a much higher level of mRNA in HE1 cells. This is in agreement with the higher level of HRR (ICAM-1) expression in HE1 cells. A second 2.4 kb RNA was also detected in HE1 cells. These data confirm that the human ICAM-1 mRNA is expressed in HRR transfectants. See FIG. 4B.

The human ICAM-1 gene was isolated from the HE1 transfectant using polymerase chain reaction (PCR) amplification utilizing the Perkin-Elmer/Cetus DNA Amplification System, Perkin Elmer, Wellesley Mass. PCR amplification was performed on single stranded cDNA made from HeLa, Ltd⁻ and HE1 RNA. Primers were made from the 5' and 3' coding regions of the published ICAM-1 sequence. ICAM-1 specific amplification products were detected by hybridization of a Southern blot of the PCR reactions using the ICAM-1 oligonucleotide. As shown in FIG. 4C, a single band of approximately 1600 bp which matches the predicted size was amplified from HeLa cells and HE1 cells but was absent from Ltk⁻ cells. The amplification product was cloned into Bluescript® (Strategene, San Diego, Calif.) and two independent clones designated PHRR1 and PHRR2 were obtained. The complete sequence of PHRR2 showed 100% identity with the published ICAM-1 coding sequence with the exception of a single G to A change previously described.

A lambda GT11 library made from randomly primed HE1 cDNA was screened with the ICAM-1 and ICAM-3 probes and eight positive clones were isolated. Six clones as shown in FIG. 7 were selected for further study and were anlayzed by partial DNA sequencing. A total of approximately 1000 nucleotides of sequence derived from these clones showed identity with the ICAM-1 sequence.

Purification and Isolation of Soluble Protein

HeLa and HE1 cells are grown under standard conditions in DMEM (Dulbecco's Modified Essential Media) with 10% Fetal Bovine Serum. Conditioned media from these cells is harvested and centrifuged or filtered to remove cells or cellular debris. The cell-membrane bound ICAM-1 is not present in the supernatant. This media is then absorbed to a monoclonal antibody-sepharose resin (the monoclonal antibody c78.4A being an example) in which the monoclonal antibody is directed to ICAM-1 or sICAM-1 and the unabsorbed proteins are washed from the resin with a physiological saline buffer, such as phosphate-buffered saline. The bound sICAM-1 is then eluted under conditions that preserve the native conformation of the protein, as described in copending application Ser. No. 262428 filed Oct. 25, 1988.

The sICAM-1 may be further purified by lectin affinity chromatography, ion exchange chromatography, or gel filtration.

mRNA transcribed in vitro from cDNA encoding sICAM in the Bluescript® vector (Strategene) was translated in vitro. In the absence of microsomal membranes, an unglycosylated protein with an apparent MW of 52,000 daltons was obtained; in the presence of microsomal membranes, a glycosylated species of 72,400 daltons was obtained which was sequestered within the microsomal membrane, indicating that the sICAM polypeptide is correctly translocated, processed, and glycosylated by the microsomal membranes.

cDNA's encoding tmICAM and sICAM in the CDM8 vector (See, B. and Aruffo, A. PNAS 84:3365 (1987) were transfected into COS cells and mouse L cells using the DEAE-dextran technique. AT 72 hr, the cells were analyzed by two methods: (1) FACS analysis with anti-ICAM Mab (c78.4) for cell membrane expression of ICAM species and (2) metabolic labeling followed by immunoabsorption with anti-ICAM Mab of cell supernatants and cell lysates. The results from the metabolic labelling indicated intracellular accumulation of a 68,000 dalton species in sICAM-transfected cells but no detectable secretion of sICAM into th supernatant. These data are consistent with sICAM being secreted through the "Regulated" secretory pathway (R. B. Kelly, Science 230:25 (1985)).

Antibody probes specific for sICAM and for ICAM-1 were prepared. The synthetic peptides S-PEP,

P P G M R L S S S L W (C) [SEQ ID NO:8]

derived from a unique 11 amino acid sequence at the C-terminus of sICAM, and P002, derived from the C-terminus of ICAM-1,

G T P M K P N T Q A T P P (C) [SEQ ID NO:9]

was made and purified; the C-terminal C residues in parentheses were added to facilitate coupling of the peptides to protein carriers. The synthetic peptide was coupled to KLH (Keyhole Limpit Hemocyanin) by standard procedures and the conjugate injected into rabbits to product anti-peptide antisera were shown to specifically bind to their respective peptide immunogens.

What is claimed is:

1. A method of recovering soluble intercellular adhesion molecule-1 (sICAM-1, having the amino acid sequence set forth in FIG. 1) in substantially pure form comprising the steps of:
(A) removing the supernatant from unlysed cells,
(B) introducing the supernatant to an affinity matrix containing immobilized antibody which binds to sICAM-1,
(C) permitting said sICAM-1 to bind to said antibody of said matrix,
(D) washing said affinity matrix to remove unbound contaminants, and
(E) recovering said sICAM-1 in substantially pure form by eluting said sICAM-1 from said matrix.

2. The method of claim 1, wherein the immobilized antibody of step (B) is selected from the group consisting of antibodies against ICAM-1 and sICAM-1.

3. The method of claim 1 further including the step of introducing the supernatant to a wheat germ agglutinin column.

4. The method of claim 3 wherein the supernatant is introduced to said wheat germ agglutinin column before the supernatant is introduced to said antibody column.

5. The method of claim 3 wherein the supernatant is introduced to said wheat germ agglutinin column after the supernatant is introduced to said antibody column.

6. The method of claim 1 or 2 additionally comprising a purification step selected from the group consisting of velocity sedimentation through sucrose gradients, sizing chromatography, gel electrophoresis, and ion chromatography.

* * * * *

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 31 bases
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL: no ( i v ) ANTI-SENSE: no ( i x ) FEATURE:
        ( A ) NAME/KEY: PCR 5.1 (5'PCR primer)
        ( B ) LOCATION: 5'end of ICAM-1 coding sequence
        ( D ) OTHER INFORMATION: bp 1 = G; bp 2-7 = EcoRI
            site; bp 8- 31 = 24 bases coding for the first
            eight amino acid residues of hICAM-1

( x ) PUBLICATION INFORMATION:

(A) AUTHORS: Greve, J.M., G. Davis, A.M. Meyer,
C.P. Forte, S.C. Yost, C.W. Marlor, M.E.
Kamarck, and A. McClelland
(B) TITLE: The Major Human Rhinovirus Receptor is
ICAM-1
(C) JOURNAL: Cell
(D) VOLUME: 56
(F) PAGES: 839-847
(G) DATE: March 10, 1989
(K) RELEVANT RESIDUES IN SEQ ID NO:1: FROM 1 TO
31

(x i) SEQUENCE DESCRIPTION: SEQ ID NO:1:

GGAATTC ATG GCT CCC AGC AGC CCC CGG CCC 31
        Met Ala Pro Ser Ser Pro Arg Pro
                          5

(2) INFORMATION FOR SEQ ID NO:2:

(i) SEQUENCE CHARACTERISTICS:
(A) LENGTH: 31 bases
(B) TYPE: nucleic acid
(C) STRANDEDNESS: single
(D) TOPOLOGY: linear (i i) MOLECULE TYPE: other nucleic acid (i i i) HYPOTHETICAL: no (i v) ANTI-SENSE: yes (i x) FEATURE:
(A) NAME/KEY: PCR 3.1 (3'PCR primer)
(B) LOCATION: 3'end of ICAM-1 coding sequence
(D) OTHER INFORMATION: base 1 =G; base 2-7 =
EcoRI site; base 8-31 = 24 bases
complementary to nucleic acid sequence coding
for last 8 amino acid residues of hICAM-1

(x) PUBLICATION INFORMATION:
(A) AUTHORS: Greve, J.M., G. Davis, A.M. Meyer,
C.P. Forte, S.C. Yost, C.W. Marlor, M.E.
Kamarck, and A. McClelland
(B) TITLE: The Major Human Rhinovirus Receptor is
ICAM-1
(C) JOURNAL: Cell
(D) VOLUME: 56
(F) PAGES: 839-847
(G) DATE: March 10, 1989
(K) RELEVANT RESIDUES IN SEQ ID NO:2: FROM 1 TO
31

(x i) SEQUENCE DESCRIPTION: SEQ ID NO:2:

GGAATTCTCA GGGAGGCGTG GCTTGTGTGT T 31

(2) INFORMATION FOR SEQ ID NO:3:

(i) SEQUENCE CHARACTERISTICS:
(A) LENGTH: 24 bases
(B) TYPE: nucleic acid
(C) STRANDEDNESS: single
(D) TOPOLOGY: linear (i i) MOLECULE TYPE: other nucleic acid (i i i) HYPOTHETICAL: no (i v) ANTI-SENSE: no (i x) FEATURE:
(A) NAME/KEY: PCR 5.4 (5'PCR primer)
(B) LOCATION: nucleotides 1351 to 1374 of sICAM (x i) SEQUENCE DESCRIPTION: SEQ ID NO:3:

CTT GAG GGC ACC TAC CTC TGT CGG 24

Leu Glu Gly Thr Tyr Leu Cys Arg
              5

( 2 ) INFORMATION FOR SEQ ID NO:4:

( i ) SEQUENCE CHARACTERISTICS:
        ( A ) LENGTH: 24 bases
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL: no ( i v ) ANTI-SENSE: yes ( i x ) FEATURE:
        ( A ) NAME/KEY: 3'PCR primer
        ( B ) LOCATION: complementary to nucleotides 1432 -
            1455 of sICAM ( x i ) SEQUENCE DESCRIPTION: SEQ ID NO:4:

AGTGATGATG ACAATCTCAT ACCG                                                                                      2 4

( 2 ) INFORMATION FOR SEQ ID NO:5:

( i ) SEQUENCE CHARACTERISTICS:
        ( A ) LENGTH: 47 bases
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL: no ( i v ) ANTI-SENSE: yes ( i x ) FEATURE:
        ( A ) NAME/KEY: ICAM1 probe
        ( B ) LOCATION: complementary to nucleotides 565 to
            611 of ICAM- 1

( x ) PUBLICATION INFORMATION:
        ( A ) AUTHORS: Greve, J.M., G. Davis, A.M. Meyer,
            C.P. Forte, S.C. Yost, C.W. Marlor, M.E.
            Kamarck, and A. McClelland
        ( B ) TITLE: The Major Human Rhinovirus Receptor is
            ICAM-1
        ( C ) JOURNAL: Cell
        ( D ) VOLUME: 56
        ( F ) PAGES: 839-847
        ( G ) DATE: March 10, 1989
        ( K ) RELEVANT RESIDUES IN SEQ ID NO:5: FROM 1 TO
            47

( x i ) SEQUENCE DESCRIPTION: SEQ ID NO:5:

GAGGTGTTCT CAAACAGCTC CAGCCCTTGG GGCCGCAGGT CCAGTTC                                          4 7

( 2 ) INFORMATION FOR SEQ ID NO:6:

( i ) SEQUENCE CHARACTERISTICS:
        ( A ) LENGTH: 47 bases
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL: no ( i v ) ANTI-SENSE: yes ( i x ) FEATURE:

(A) NAME/KEY: ICAM3 probe
                (B) LOCATION: complementary to nucleotides 602 to
                    648 of human ICAM (x) PUBLICATION INFORMATION:
                (A) AUTHORS: Greve, J.M., G. Davis, A.M. Meyer,
                    C.P. Forte, S.C. Yost, C.W. Marlor, M.E.
                    Kamarck, and A. McClelland
                (B) TITLE: The Major Human Rhinovirus Receptor is
                    ICAM-1
                (C) JOURNAL: Cell
                (D) VOLUME: 56
                (F) PAGES: 839-847
                (G) DATE: March 10, 1989
                (K) RELEVANT RESIDUES IN SEQ ID NO:6: FROM 1 TO
                    47

(xi) SEQUENCE DESCRIPTION: SEQ ID NO:6:

CGTTGGCAGG ACAAAGGTCT GGAGCTGGTA GGGGGCCGAG GTGTTCT                                    47

(2) INFORMATION FOR SEQ ID NO:7:

(i) SEQUENCE CHARACTERISTICS:
                (A) LENGTH: 34 bases
                (B) TYPE: nucleic acid
                (C) STRANDEDNESS: single
                (D) TOPOLOGY: linear (ii) MOLECULE TYPE: other nucleic acid (iii) HYPOTHETICAL: no (iv) ANTI-SENSE: yes (ix) FEATURE:
                (A) NAME/KEY: PCR 3.2 antisense
                (D) OTHER INFORMATION: base 1 =G; bases 2-7 =
                    EcoR1 site; bases 8-10 = complementary to a stop
                    codon; bases 11-34 = 24 bases complementary to
                    nucleotides 1474-1497 of ICAM-1, nucleotide 1 being
                    the ATG (xi) SEQUENCE DESCRIPTION: SEQ ID NO:7:

GGAATTCTCA CTCATACCGG GGGGAGAGCA CATT                                                  34

(2) INFORMATION FOR SEQ ID NO:8:

(i) SEQUENCE CHARACTERISTICS:
                (A) LENGTH: 12 amino acid residues
                (B) TYPE: amino acid
                (D) TOPOLOGY: linear (ii) MOLECULE TYPE:
                (A) DESCRIPTION: peptide (iii) HYPOTHETICAL: no (v) FRAGMENT TYPE: modified C-terminal fragment (ix) FEATURE:
                (A) NAME/KEY: modified sICAM fragment
                (B) LOCATION: C-terminus of sICAM
                (D) OTHER INFORMATION: first 11 amino acids
                    correspond to C-terminus of sICAM; last
                    residue (Cys) added to faciliate coupling (xi) SEQUENCE DESCRIPTION: SEQ ID NO:8:

Pro Pro Gly Met Arg Leu Ser Ser Ser Leu Trp Cys
                  5                   10

(2) INFORMATION FOR SEQ ID NO:9:

(i) SEQUENCE CHARACTERISTICS:
                (A) LENGTH: 14 amino acid residues ( B ) TYPE: amino acid
( D ) TOPOLOGY: linear ( i i ) MOLECULE TYPE:
( A ) DESCRIPTION: peptide ( i i i ) HYPOTHETICAL: no ( v ) FRAGMENT TYPE: C-terminal fragment ( i x ) FEATURE:
( A ) NAME/KEY: modified ICAM fragment
( B ) LOCATION: C-terminus
( D ) OTHER INFORMATION: first 11 amino acid
residues correspond to the C-terminus of
ICAM; last residue (Cys) added to facilitate
coupling ( x i ) SEQUENCE DESCRIPTION: SEQ ID NO:9:

| Gly | Thr | Pro | Met | Lys | Pro | Asn | Thr | Gln | Ala | Thr | Pro | Pro | Cys |
|-----|-----|-----|-----|-----|-----|-----|-----|-----|-----|-----|-----|-----|-----|
|     |     |     |     | 5   |     |     |     |     | 10  |     |     |     |     |

( 2 ) INFORMATION FOR SEQ ID NO:10:

( i ) SEQUENCE CHARACTERISTICS:
( A ) LENGTH: 1443 bases
( B ) TYPE: nucleic acid
( C ) STRANDEDNESS: single
( D ) TOPOLOGY: linear ( i i ) MOLECULE TYPE: cDNA to mRNA ( i i i ) HYPOTHETICAL: no ( i v ) ANTI-SENSE: no ( v i ) ORIGINAL SOURCE:
( A ) ORGANISM: human
( G ) CELL TYPE: epithelial
( H ) CELL LINE: HeLa ( v i i ) IMMEDIATE SOURCE:
( A ) LIBRARY: cDNA library ( i x ) FEATURE:
( A ) NAME/KEY: human sICAM cDNA to mRNA sequence
( B ) LOCATION: nucleotides 1 to 1435 numbered
beginning at ATG coding for first Met of
human sICAM protein ( x i ) SEQUENCE DESCRIPTION: SEQ ID NO:10:

| ATG | GCT | CCC | AGC | AGC | CCC | CGG | CCC | GCG | CTG | CCC | GCA | CTC | CTG | GTC | 45 |
|-----|-----|-----|-----|-----|-----|-----|-----|-----|-----|-----|-----|-----|-----|-----|----|
| Met | Ala | Pro | Ser | Ser | Pro | Arg | Pro | Ala | Leu | Pro | Ala | Leu | Leu | Val |    |
|     |     |     |     | 5   |     |     |     |     | 10  |     |     |     |     | 15  |    |

| CTG | CTC | GGG | GCT | CTG | TTC | CCA | GGA | CCT | GGC | AAT | GCC | CAG | ACA | TCT | 90 |
|-----|-----|-----|-----|-----|-----|-----|-----|-----|-----|-----|-----|-----|-----|-----|----|
| Leu | Leu | Gly | Ala | Leu | Phe | Pro | Gly | Pro | Gly | Asn | Ala | Gln | Thr | Ser |    |
|     |     |     |     | 20  |     |     |     |     | 25  |     |     |     |     | 30  |    |

| GTG | TCC | CCC | TCA | AAA | GTC | ATC | CTG | CCC | CGG | GGA | GGC | TCC | GTG | CTG | 135 |
|-----|-----|-----|-----|-----|-----|-----|-----|-----|-----|-----|-----|-----|-----|-----|-----|
| Val | Ser | Pro | Ser | Lys | Val | Ile | Leu | Pro | Arg | Gly | Gly | Ser | Val | Leu |     |
|     |     |     |     | 35  |     |     |     |     | 40  |     |     |     |     | 45  |     |

| GTG | ACA | TGC | AGC | ACC | TCC | TGT | GAC | CAG | CCC | AAG | TTG | TTG | GGC | ATA | 180 |
|-----|-----|-----|-----|-----|-----|-----|-----|-----|-----|-----|-----|-----|-----|-----|-----|
| Val | Thr | Cys | Ser | Thr | Ser | Cys | Asp | Gln | Pro | Lys | Leu | Leu | Gly | Ile |     |
|     |     |     |     | 50  |     |     |     |     | 55  |     |     |     |     | 60  |     |

| GAG | ACC | CCG | TTG | CCT | AAA | AAG | GAG | TTG | CTC | CTG | CCT | GGG | AAC | AAC | 225 |
|-----|-----|-----|-----|-----|-----|-----|-----|-----|-----|-----|-----|-----|-----|-----|-----|
| Glu | Thr | Pro | Leu | Pro | Lys | Lys | Glu | Leu | Leu | Leu | Pro | Gly | Asn | Asn |     |
|     |     |     |     | 65  |     |     |     |     | 70  |     |     |     |     | 75  |     |

| CGG | AAG | GTG | TAT | GAA | CTG | AGC | AAT | GTG | CAA | GAA | GAT | AGC | CAA | CCA | 270 |
|-----|-----|-----|-----|-----|-----|-----|-----|-----|-----|-----|-----|-----|-----|-----|-----|
| Arg | Lys | Val | Tyr | Glu | Leu | Ser | Asn | Val | Gln | Glu | Asp | Ser | Gln | Pro |     |
|     |     |     |     | 80  |     |     |     |     | 85  |     |     |     |     | 90  |     |

| ATG | TGC | TAT | TCA | AAC | TGC | CCT | GAT | GGG | CAG | TCA | ACA | GCT | AAA | ACC | 315 |
|-----|-----|-----|-----|-----|-----|-----|-----|-----|-----|-----|-----|-----|-----|-----|-----|
| Met | Cys | Tyr | Ser | Asn | Cys | Pro | Asp | Gly | Gln | Ser | Thr | Ala | Lys | Thr |     |

|     |     |     |     |     |     |     |     |     |     |     |     |     |     |     |      |
|-----|-----|-----|-----|-----|-----|-----|-----|-----|-----|-----|-----|-----|-----|-----|------|
|     |     |     |     | 95  |     |     |     |     | 100 |     |     |     |     | 105 |      |
| TTC | CTC | ACC | GTG | TAC | TGG | ACT | CCA | GAA | CGG | GTG | GAA | CTG | GCA | CCC | 360  |
| Phe | Leu | Thr | Val | Tyr | Trp | Thr | Pro | Glu | Arg | Val | Glu | Leu | Ala | Pro |      |
|     |     |     |     | 110 |     |     |     |     | 115 |     |     |     |     | 120 |      |
| CTC | CCC | TCT | TGG | CAG | CCA | GTG | GGC | AAG | AAC | CTT | ACC | CTA | CGC | TGC | 405  |
| Leu | Pro | Ser | Trp | Gln | Pro | Val | Gly | Lys | Asn | Leu | Thr | Leu | Arg | Cys |      |
|     |     |     |     | 125 |     |     |     |     | 130 |     |     |     |     | 135 |      |
| CAG | GTG | GAG | GGT | GGG | GCA | CCC | CGG | GCC | AAC | CTC | ACC | GTG | GTG | CTG | 450  |
| Gln | Val | Glu | Gly | Gly | Ala | Pro | Arg | Ala | Asn | Leu | Thr | Val | Val | Leu |      |
|     |     |     |     | 140 |     |     |     |     | 145 |     |     |     |     | 150 |      |
| CTC | CGT | GGG | GAG | AAG | GAG | CTG | AAA | CGG | GAG | CCA | GCT | GTG | GGG | GAG | 495  |
| Leu | Arg | Gly | Glu | Lys | Glu | Leu | Lys | Arg | Glu | Pro | Ala | Val | Gly | Glu |      |
|     |     |     |     | 155 |     |     |     |     | 160 |     |     |     |     | 165 |      |
| CCC | GCT | GAG | GTC | ACG | ACC | ACG | GTG | CTG | GTG | AGG | AGA | GAT | CAC | CAT | 540  |
| Pro | Ala | Glu | Val | Thr | Thr | Thr | Val | Leu | Val | Arg | Arg | Asp | His | His |      |
|     |     |     |     | 170 |     |     |     |     | 175 |     |     |     |     | 180 |      |
| GGA | GCC | AAT | TTC | TCG | TGC | CGC | ACT | GAA | CTG | GAC | CTG | CGG | CCC | CAA | 585  |
| Gly | Ala | Asn | Phe | Ser | Cys | Arg | Thr | Glu | Leu | Asp | Leu | Arg | Pro | Gln |      |
|     |     |     |     | 185 |     |     |     |     | 190 |     |     |     |     | 195 |      |
| GGG | CTG | GAG | CTG | TTT | GAG | AAC | ACC | TCG | GCC | CCC | TAC | CAG | CTC | CAG | 630  |
| Gly | Leu | Glu | Leu | Phe | Glu | Asn | Thr | Ser | Ala | Pro | Tyr | Gln | Leu | Gln |      |
|     |     |     |     | 200 |     |     |     |     | 205 |     |     |     |     | 210 |      |
| ACC | TTT | GTC | CTG | CCA | GCG | ACT | CCC | CCA | CAA | CTT | GTC | AGC | CCC | CGG | 675  |
| Thr | Phe | Val | Leu | Pro | Ala | Thr | Pro | Pro | Gln | Leu | Val | Ser | Pro | Arg |      |
|     |     |     |     | 215 |     |     |     |     | 220 |     |     |     |     | 225 |      |
| GTC | CTA | GAG | GTG | GAC | ACG | CAG | GGG | ACC | GTG | GTC | TGT | TCC | CTG | GAC | 720  |
| Val | Leu | Glu | Val | Asp | Thr | Gln | Gly | Thr | Val | Val | Cys | Ser | Leu | Asp |      |
|     |     |     |     | 230 |     |     |     |     | 235 |     |     |     |     | 240 |      |
| GGG | CTG | TTC | CCA | GTC | TCG | GAG | GCC | CAG | GTC | CAC | CTG | GCA | CTG | GGG | 765  |
| Gly | Leu | Phe | Pro | Val | Ser | Glu | Ala | Gln | Val | His | Leu | Ala | Leu | Gly |      |
|     |     |     |     | 245 |     |     |     |     | 250 |     |     |     |     | 255 |      |
| GAC | CAG | AGG | TTG | AAC | CCC | ACA | GTC | ACC | TAT | GGC | AAC | GAC | TCC | TTC | 810  |
| Asp | Gln | Arg | Leu | Asn | Pro | Thr | Val | Thr | Tyr | Gly | Asn | Asp | Ser | Phe |      |
|     |     |     |     | 260 |     |     |     |     | 265 |     |     |     |     | 270 |      |
| TCG | GCC | AAG | GCC | TCA | GTC | AGT | GTG | ACC | GCA | GAG | GAC | GAG | GGC | ACC | 855  |
| Ser | Ala | Lys | Ala | Ser | Val | Ser | Val | Thr | Ala | Glu | Asp | Glu | Gly | Thr |      |
|     |     |     |     | 275 |     |     |     |     | 280 |     |     |     |     | 285 |      |
| CAG | CGG | CTG | ACG | TGT | GCA | GTA | ATA | CTG | GGG | AAC | CAG | AGC | CAG | GAG | 900  |
| Gln | Arg | Leu | Thr | Cys | Ala | Val | Ile | Leu | Gly | Asn | Gln | Ser | Gln | Glu |      |
|     |     |     |     | 290 |     |     |     |     | 295 |     |     |     |     | 300 |      |
| ACA | CTG | CAG | ACA | GTG | ACC | ATC | TAC | AGC | TTT | CCG | GCG | CCC | AAC | GTG | 945  |
| Thr | Leu | Gln | Thr | Val | Thr | Ile | Tyr | Ser | Phe | Pro | Ala | Pro | Asn | Val |      |
|     |     |     |     | 305 |     |     |     |     | 310 |     |     |     |     | 315 |      |
| ATT | CTG | ACG | AAG | CCA | GAG | GTC | TCA | GAA | GGG | ACC | GAG | GTG | ACA | GTG | 990  |
| Ile | Leu | Thr | Lys | Pro | Glu | Val | Ser | Glu | Gly | Thr | Glu | Val | Thr | Val |      |
|     |     |     |     | 320 |     |     |     |     | 325 |     |     |     |     | 330 |      |
| AAG | TGT | GAG | GCC | CAC | CCT | AGA | GCC | AAG | GTG | ACG | CTG | AAT | GGG | GTT | 1035 |
| Lys | Cys | Glu | Ala | His | Pro | Arg | Ala | Lys | Val | Thr | Leu | Asn | Gly | Val |      |
|     |     |     |     | 335 |     |     |     |     | 340 |     |     |     |     | 345 |      |
| CCA | GCC | CAG | CCA | CTG | GGC | CCG | AGG | GCC | CAG | CTC | CTG | CTG | AAG | GCC | 1080 |
| Pro | Ala | Gln | Pro | Leu | Gly | Pro | Arg | Ala | Gln | Leu | Leu | Leu | Lys | Ala |      |
|     |     |     |     | 350 |     |     |     |     | 355 |     |     |     |     | 360 |      |
| ACC | CCA | GAG | GAC | AAC | GGG | CGC | AGC | TTC | TCC | TGC | TCT | GCA | ACC | CTG | 1125 |
| Thr | Pro | Glu | Asp | Asn | Gly | Arg | Ser | Phe | Ser | Cys | Ser | Ala | Thr | Leu |      |
|     |     |     |     | 365 |     |     |     |     | 370 |     |     |     |     | 375 |      |
| GAG | GTG | GCC | GGC | CAG | CTT | ATA | CAC | AAG | AAC | CAG | ACC | CGG | GAG | CTT | 1170 |
| Glu | Val | Ala | Gly | Gln | Leu | Ile | His | Lys | Asn | Gln | Thr | Arg | Glu | Leu |      |
|     |     |     |     | 380 |     |     |     |     | 385 |     |     |     |     | 390 |      |
| CGT | GTC | CTG | TAT | GGC | CCC | CGA | CTG | GAC | GAG | AGG | GAT | TGT | CCG | GGA | 1215 |
| Arg | Val | Leu | Tyr | Gly | Pro | Arg | Leu | Asp | Glu | Arg | Asp | Cys | Pro | Gly |      |

|     |     |     |     |     |     |     |     |     |     |     |     |     |     |      |
|-----|-----|-----|-----|-----|-----|-----|-----|-----|-----|-----|-----|-----|-----|------|
|     |     |     |     | 395 |     |     |     | 400 |     |     |     | 405 |     |      |
| AAC | TGG | ACG | TGG | CCA | GAA | AAT | TCC | CAG | CAG | ACT | CCA | ATG | TGC | CAG  | 1260 |
| Asn | Trp | Thr | Trp | Pro | Glu | Asn | Ser | Gln | Gln | Thr | Pro | Met | Cys | Gln  |
|     |     |     |     | 410 |     |     |     | 415 |     |     |     |     |     | 420  |
| GCT | TGG | GGG | AAC | CCA | TTG | CCC | GAG | CTC | AAG | TGT | CTA | AAG | GAT | GGC  | 1305 |
| Ala | Trp | Gly | Asn | Pro | Leu | Pro | Glu | Leu | Lys | Cys | Leu | Lys | Asp | Gly  |
|     |     |     |     | 425 |     |     |     | 430 |     |     |     |     |     | 435  |
| ACT | TTC | CCA | CTG | CCC | ATC | GGG | GAA | TCA | GTG | ACT | GTC | ACT | CGA | GAT  | 1350 |
| Thr | Phe | Pro | Leu | Pro | Ile | Gly | Glu | Ser | Val | Thr | Val | Thr | Arg | Asp  |
|     |     |     |     | 440 |     |     |     | 445 |     |     |     |     |     | 450  |
| CTT | GAG | GGC | ACC | TAC | CTC | TGT | CGG | GCC | AGG | AGC | ACT | CAA | GGG | GAG  | 1395 |
| Leu | Glu | Gly | Thr | Tyr | Leu | Cys | Arg | Ala | Arg | Ser | Thr | Gln | Gly | Glu  |
|     |     |     |     | 455 |     |     |     | 460 |     |     |     |     |     | 465  |
| GTC | ACC | CGC | AAG | CCC | CCC | GGT | ATG | AGA | TTG | TCA | TCA | TCA | CTG | TGG  | 1440 |
| Val | Thr | Arg | Lys | Pro | Pro | Gly | Met | Arg | Leu | Ser | Ser | Ser | Leu | Trp  |
|     |     |     |     | 470 |     |     |     | 475 |     |     |     |     |     | 480  |
| TAG |     |     |     |     |     |     |     |     |     |     |     |     |     |      | 1443 |

(2) INFORMATION FOR SEQ ID NO:11:

(i) SEQUENCE CHARACTERISTICS:
        (A) LENGTH: 240 bases
        (B) TYPE: nucleic acid
        (C) STRANDEDNESS: single
        (D) TOPOLOGY: linear (ii) MOLECULE TYPE: cDNA to mRNA (iii) HYPOTHETICAL: no (iv) ANTI-SENSE: no (vi) ORIGINAL SOURCE:
        (A) ORGANISM: human
        (G) CELL TYPE: epithelial
        (H) CELL LINE: HeLa (vii) IMMEDIATE SOURCE:
        (A) LIBRARY: cDNA library (ix) FEATURE:
        (A) NAME/KEY: partial human ICAM cDNA to mRNA
            sequence
        (B) LOCATION: nucleotides 1384 to 1623 numbered
            beginning at ATG coding for first Met of
            human ICAM protein (x) PUBLICATION INFORMATION:
        (A) AUTHORS: Greve, J.M., G. Davis, A.M. Meyer,
            C.P. Forte, S.C. Yost, C.W. Marlor, M.E.
            Kamarck, and A. McClelland
        (B) TITLE: The Major Human Rhinovirus Receptor is
            ICAM-1
        (C) JOURNAL: Cell
        (D) VOLUME: 56
        (F) PAGES: 839-847
        (G) DATE: March 10, 1989
        (K) RELEVANT RESIDUES IN SEQ ID NO:11: FROM 1 TO
            240

(xi) SEQUENCE DESCRIPTION: SEQ ID NO:11:

| ACT | CAA | GGG | GAG | GTC | ACC | CGC | AAG | GTG | ACC | GTG | AAT | GTG | CTC | TCC | 45 |
|-----|-----|-----|-----|-----|-----|-----|-----|-----|-----|-----|-----|-----|-----|-----|----|
| Thr | Gln | Gly | Glu | Val | Thr | Arg | Lys | Val | Thr | Val | Asn | Val | Leu | Ser |
|     |     |     |     | 5   |     |     |     | 10  |     |     |     |     |     | 15  |
| CCC | CGG | TAT | GAG | ATT | GTC | ATC | ATC | ACT | GTG | GTA | GCA | GCC | GCA | GTC | 90 |
| Pro | Arg | Tyr | Glu | Ile | Val | Ile | Ile | Thr | Val | Val | Ala | Ala | Ala | Val |
|     |     |     |     | 20  |     |     |     | 25  |     |     |     |     |     | 30  |
| ATA | ATG | GGC | ACT | GCA | GGC | CTC | AGC | ACG | TAC | CTC | TAT | AAC | CGC | CAG | 135 |
| Ile | Met | Gly | Thr | Ala | Gly | Leu | Ser | Thr | Tyr | Leu | Tyr | Asn | Arg | Gln |
|     |     |     |     | 35  |     |     |     | 40  |     |     |     |     |     | 45  |

```
CGG  AAG  ATC  AAG  AAA  TAC  AGA  CTA  CAA  CAG  GCC  CAA  AAA  GGG  ACC              180
Arg  Lys  Ile  Lys  Lys  Tyr  Arg  Leu  Gln  Gln  Ala  Gln  Lys  Gly  Thr
                         50                      55                      60

CCC  ATG  AAA  CCG  AAC  ACA  CAA  GCC  ACG  CCT  CCC  TGAACCTATC                       223
Pro  Met  Lys  Pro  Asn  Thr  Gln  Ala  Thr  Pro  Pro
                         65                      70

CCGGGACAGG  GCCTCTT                                                                      240
```

( 2 ) INFORMATION FOR SEQ ID NO:12:

( i ) SEQUENCE CHARACTERISTICS:
           ( A ) LENGTH: 221 bases
           ( B ) TYPE: nucleic acid
           ( C ) STRANDEDNESS: single
           ( D ) TOPOLOGY: linear ( i i ) MOLECULE TYPE: cDNA to mRNA ( i i i ) HYPOTHETICAL: no ( i v ) ANTI-SENSE: no ( v i ) ORIGINAL SOURCE:
           ( A ) ORGANISM: human
           ( G ) CELL TYPE: epithelial
           ( H ) CELL LINE: HeLa ( v i i ) IMMEDIATE SOURCE:
           ( A ) LIBRARY: cDNA library ( i x ) FEATURE:
           ( A ) NAME/KEY: partial human sICAM-1 cDNA to mRNA
               sequence
           ( B ) LOCATION: sequence from human sICAM
               corresponding to nucleotides 1384 to 1623 of
               human ICAM lacking bp 1407 to 1426,
               inclusive, of hICAM ( x i ) SEQUENCE DESCRIPTION: SEQ ID NO:12:

```
ACT  CAA  GGG  GAG  GTC  ACC  CGC  AAG  CCC  CCC  GGT  ATG  AGA  TTG  TCA               45
Thr  Gln  Gly  Glu  Val  Thr  Arg  Lys  Pro  Pro  Gly  Met  Arg  Leu  Ser
                         5                       10                      15

TCA  TCA  CTG  TGG  TAGCAGCCGC  AGTCATAATG  GGCACTGCAG  GCCTCAGCAC                       97
Ser  Ser  Leu  Trp

GTACCTCTAT  AACCGCCAGC  GGAAGATCAA  GAAATACAGA  CTACAACAGG                              147

CCCAAAAAGG  GACCCCCATG  AAACCGAACA  CACAAGCCAC  GCCTCCCTGA                              197

ACCTATCCCG  GGACAGGGCC  TCTT                                                            221
```